United States Patent [19]

Egan et al.

[11] 4,343,726

[45] * Aug. 10, 1982

[54] LOW IRRITATING HIGH VISCOSITY DETERGENT COMPOSITION

[75] Inventors: Richard R. Egan, Worthington; Phillip L. Cotrell, Urbana, both of Ohio

[73] Assignee: Sherex Chemical Company, Inc., Dublin, Ohio

[ * ] Notice: The portion of the term of this patent subsequent to Jan. 27, 1998, has been disclaimed.

[21] Appl. No.: 119,260

[22] Filed: Feb. 7, 1980

Related U.S. Application Data

[63] Continuation-in-part of Ser. No. 36,706, May 7, 1979, Pat. No. 4,247,425, which is a continuation of Ser. No. 742,075, Sep. 13, 1978, abandoned, which is a continuation-in-part of Ser. No. 848,978, Nov. 7, 1977, abandoned, and a continuation-in-part of Ser. No. 49,835, Jun. 18, 1979, Pat. No. 4,256,611, which is a continuation of Ser. No. 942,074, Sep. 13, 1978, abandoned, which is a continuation-in-part of Ser. No. 795,342, May 9, 1977, abandoned.

[51] Int. Cl.$^3$ .......................... C11D 1/12; C11D 1/83

[52] U.S. Cl. ........................ 252/547; 252/174.21; 252/548; 252/550; 252/551; 252/554; 252/558; 252/559; 252/DIG. 1; 252/DIG. 13; 252/DIG. 14

[58] Field of Search .................... 252/174.21, 174.22, 252/545, 548, 550, 547, 551, 554, 558, 559, DIG. 1, DIG. 14, DIG. 13

[56] References Cited

U.S. PATENT DOCUMENTS

| | | | |
|---|---|---|---|
| 3,928,251 | 12/1975 | Bolich et al. ...................... | 252/545 |
| 3,950,417 | 4/1976 | Verdicchio et al. ................. | 252/545 |
| 4,002,579 | 1/1977 | Mizutani et al. .................... | 252/544 |
| 4,177,171 | 12/1979 | Walts .................................. | 252/541 |

FOREIGN PATENT DOCUMENTS

| | | |
|---|---|---|
| 2457927 | 6/1975 | Fed. Rep. of Germany . |
| 46-14340 | 4/1971 | Japan . |
| 46-66506 | 6/1977 | Japan . |

*Primary Examiner*—P. E. Willis, Jr.
*Attorney, Agent, or Firm*—Pollock, Vande Sande & Priddy

[57] ABSTRACT

A detergent composition having low eye and skin irritation properties and capable of forming a high viscosity composition in water which includes an adduct of ethylene oxide or mixtures of ethylene oxide and propylene oxide and a glycerol ester of certain carboxylic acids; and an anionic surface active agent.

56 Claims, No Drawings

LOW IRRITATING HIGH VISCOSITY DETERGENT COMPOSITION

CROSS-REFERENCE TO RELATED APPLICATIONS

The present application is a continuation-in-part of application Ser. No. 36,706, filed May 7, 1979, now U.S. Pat. No. 4,247,425, which is a continuation of application Ser. No. 742,075, filed Sept. 13, 1978, now abandoned, which in turn is a continuation-in-part of application Ser. No. 848,978, filed Nov. 7, 1977, now abandoned, and is a continuation-in-part of application Ser. No. 49,835, filed June 18, 1979, now U.S. Pat. No. 4,256,611, which in turn is a continuation of application Ser. No. 942,074, filed Sept. 13, 1978, now abandoned, which in turn is a continuation-in-part of application Ser. No. 795,342, filed May 9, 1977, and now abandoned.

DESCRIPTION

Technical Field

The present invention is directed to detergent compositions which exhibit low eye and skin irritation characteristics along with providing high viscosity composition in liquids such as water. In particular, the present invention is concerned with low irritation, high lathering detergent gels and concentrates which disperse readily into water and exhibit high viscosity. The compositions of the present invention are especially suitable for hair shampoos and especially for the socalled baby detergents, such as baby hair shampoos, where mildness with respect to eye and skin irritation is essential.

Background Art

Many prior detergents have been based on the combination of an anionic surface active agent and another surface active agent serving as a foam promoter or stabilizer. Some examples of anionic surface active agents employed in detergents include sodium lauryl sulfate (SLS), sodium lauryl ether sulfate (SLES) and linear alkyl benzene sulfonate (LAS). Generally, the foam promoter is a tertiary amine oxide or an alkanolamide, either of the so-called superamide, or of the Kritchevsky type. The superamides refer generally to those containing concentrations of about 90–95% amide and prepared by reacting a carboxylic fatty acid ester, such as a methyl ester with an alkanolamine, such as diethanolamine in about 1:1 mole ratio. Those of the Kritchevsky type generally refer to amides having about a 65% amide concentration and prepared from a fatty acid and alkanolamine, such as diethanolamine in mole ratio of about 1:2. However, all of the above-mentioned surface active agents, and especially the anionic surface active agents, are severe eye irritants and are capable of causing mild to moderate skin irritation to some sensitive individuals.

In recent years, attempts have been made towards substantially ameliorating the irritant effects of such compositions. For instance, it has been suggested to use an anionic surface active agent in conjunction with an amphoteric type surface active agent and to combine these compounds with certain nonionic surface active agents, such as an ethoxylate of a partial sorbitol monoester of certain carboxylic fatty acids, such as lauric acid and palmitic acid as exemplified by U.S. Pat. No. 3,950,417. Moreover, low irritation detergents and shampoos are now commercially available which include an anionic surface active agent in combination with certain ethoxylated glycerol monococoate nonionic surface active agents commercially available under the trade designation Varonic LI63 and Varonic LI67 from Sherex Chemical Co., Inc., the assignee of the present application. Although these latter compositions exhibit minimal eye irritation properties along with the ability to extensively vary the viscosity of dilute aqueous solutions thereof, such are not available in formulations without auxiliary thickening agents which produce systems having viscosities of 10,000 centipoises and above and are not available in gel form.

Attempts to provide non-irritating detergent compositions with increased viscosities have been reported. For instance, Belgium Pat. No. 847,944 to Johnson and Johnson suggests a non-irritating detergent composition which contains about 5 to 20% by weight of an amphoteric anionic surface active agent of a certain specified formulation along with 8 to 20% by weight of a monoester of a C16 to C18 fatty acid and sorbitan which has been reacted with 60 to 100 molar proportions of ethylene oxide. The viscosity, however, of such compositions is still only about 4,000 centipoises.

Other attempts to regulate the viscosity includes the addition of salt (sodium chloride) to the composition. However, this method is not suitable since the salt significantly increases the eye irritation properties of the product.

DISCLOSURE OF INVENTION

The present invention provides liquid detergent compositions and especially shampoos which exhibit improved eye irritation properties along with the ability to provide high viscosity aqueous compositions. The ability to achieve high viscosities and to achieve a desired control of such viscosities is obtained without the need of common salt as used in prior compositions. Moreover, the present invention makes it possible to obtain viscosities of at least 10,000 centipoises and such can be achieved without the aid of other thickening agents and without the presence of any amphoteric surface active agent. In addition, the above characteristics of low irritation and high viscosity are achieved while still maintaining good dispersability and lathering properties which are essential for compositions employed as shampoos. The compositions of the present invention when in gel form can be readily dispensed via a squeeze tube and are readily dispersable upon application to wet hair or water. In addition, the extremely low irritation properties are still present.

The detergent compositions of the present invention contain an adduct of ethylene oxide or mixtures of ethylene oxide and propylene oxide and a partial glycerol ester of a carboxylic fatty acid; and an anionic surface active agent. The weight ratio of the ethylene oxide adduct to the anionic surface active agent is about 1:1 to about 4:1. The partial glycerol ester has a monoglyceride content from about 15 to about 45 weight percent with diglyceride essentially constituting the balance. When the composition contains a foam promoter, such as an alkanolamide or amine oxide, the weight ratio of the ethylene oxide adduct to the total of the anionic surface active agent and foam promoter is about 1:1 to about 5:1. In addition, at least about 50% by weight of the glycerol ester is from carboxylic fatty acids having at least 16 carbon atoms. When the adduct is obtained from ethylene oxide or mixtures of ethylene oxide and propylene oxide which are substantially ethylene oxide (i.e. containing at least about 85 mole percent of ethylene oxide of the total moles of ethylene oxide and propylene oxide), at least about 50 moles of ethylene oxide per mole of the glycerol ester are employed. When the adduct is obtained from a mixture of ethylene oxide and propylene oxide having less than 85 mole percent of ethylene oxide, such as in mole ratios of ethylene oxide to propylene oxide of about 4.5 or less to 1, at least about 70 moles of ethylene oxide per mole of the glycerol ester are employed. The present invention is also concerned with aqueous compositions containing the above constituents which compositions have a viscosity of at least about 10,000 centipoises at normal room temperature.

BEST AND VARIOUS MODES FOR CARRYING OUT INVENTION

The nonionic surface active agents employed according to the present invention are derived from partial glycerol esters of higher fatty acids wherein at least about 50% by weight of the fatty acid has at least 16 carbon atoms. The applicable higher fatty acids employed in the present invention can be saturated and/or ethylenically unsaturated, and preferably are saturated and are of the so-called detergent grade. It is essential that at least about 50% by weight of the fatty acids have at least 16 carbon atoms and preferably at least 18 carbon atoms in order to achieve the high viscosity characteristics obtained by the present invention. Generally, the fatty acids employed have carbon atoms no greater than 22 carbon atoms and preferably no greater than 18 carbon atoms. The preferred fatty acids are those with compositions the same as or similar to those obtained from tallow and preferably from hydrogenated tallow. It is essential to the practice of the present invention that at least 50% by weight of the fatty acid employed contain at least 16 of carbon atoms and preferably at least 18 carbon atoms. The use of esters from mixtures of fatty acids having less than 50% by weight of acids of at least 16 carbon atoms does not result in the extremely high viscosity characteristics achieved by the present invention. For example, the use of the ethoxylated glycerol esters of coconut oil does not achieve the extremely high viscosities obtained by the present invention. The amount of esters from fatty acids which acids contain 16 or more carbon atoms in coconut oil is significantly less than 50% by weight in coconut oil. The esters are mainly those of acids which contain 12 carbon atoms. In addition, it is essential to achieving the very high viscosities obtained by the present invention to employ monoglycerides and diglycerides are contrasted to other polyhydric alcohol esters, such as sorbitan esters.

The partial esters of the present invention consist essentially of a mixture of monoglycerides and diglycerides. The partial esters generally have a monoglyceride content of about 15 to about 45% by weight, and preferably the monoglyceride content ($\alpha$, $\beta$) ranges from about 25 to about 35% by weight. As indicated above, the balance of the partial ester product will be predominantly the corresponding diglyceride.

These mono- and diglyceride mixtures can be readily prepared by the glycerolysis to a triglyceride in the presence of a basic catalyst, preferably an alkaline metal hydroxide. Alternatively, such can be prepared by directly esterifying glycerine with the fatty acids. The molar ratio of triglyceride to glycerine can be adjusted in carrying out the preferred glycerolysis method to result in a reaction product having a monoglyceride content of the amount discussed hereinabove. In accordance with this procedure, a mole of the triglyceride is transesterified with slightly in excess of one mole of glycerine to yield a product having the preferred monoglyceride content.

The nonionic surface active agents employed according to the present invention are the ethylene oxide adducts of the partial glyceride esters described hereinabove or are the adducts of said esters with a mixture of ethylene oxide and propylene oxide. The preferred nonionic surface active agents employed according to the present invention are the ethylene oxide adducts of the partial glycerol adducts described hereinabove.

When the adduct is obtained from ethylene oxide or mixtures of ethylene oxide and propylene oxide which are substantially ethylene oxide (i.e. containing at least about 85 mole percent of ethylene oxide of the total moles of ethylene oxide and propylene oxide), at least about 50 moles, preferably at least about 60 moles, more preferably at least about 80 moles, and most preferably more than about 100 moles of ethylene oxide per mole of the glycerol ester are employed.

When the adduct is obtained from a mixture of ethylene oxide and propylene oxide having less than 85 mole percent of ethylene oxide, such as in mole ratios of ethylene oxide to propylene oxide of about 4.5 or less to 1, respectively, at least about 70 moles, preferably at least about 80 moles, and most preferably more than 100 moles of ethylene oxide per mole of the glycerol ester are employed.

When mixtures of ethylene oxide and propylene oxide are employed, the mole ratio of ethylene oxide to propylene oxide is generally at least about 2:1, and preferably at least about 3:1. Also, generally such mixtures employ the ethylene oxide to propylene oxide in a mole ratio of up to about 4.5:1.

Generally up to about 1000 moles of the ethylene oxide per mole of the glycerol ester are employed. Preferably up to about 500 moles and most preferably up to about 200 moles of the ethylene oxide per mole of glycerol ester are employed. The alkoxylation is carried out be mixing the alkylene oxide and glycerol ester and carrying out the reaction preferably in the presence of a suitable catalyst, such as an alkali metal hydroxide at temperatures generally in the order of about 150° to 180° C. The reaction is ordinarily conducted in a closed system at pressures from about 2 to about 10 atmospheres. When mixtures of ethylene and propylene oxide are employed, preferably such are prepared by simultaneously adding both oxides in the selected ratio to the partial ester upon effecting the adduction reaction. Alternatively, when using mixtures of the alkylene oxides, such can be employed as a preformed mixture, and/or as a copolymer (e.g., random and/or block polymers).

The anionic surface active agents employed according to the present invention can be any anionic surface active agent and particularly those which have been used in shampoo compositions, and, accordingly, a further discussion thereof is not deemed necessary herein. Some preferred anionic surface active agents are salts of higher alkyl sulfates, salts of higher alkyl ether sulfates, salts of higher alkyl benzene sulfonates, and salts of higher alkyl sulfonates. The salts are preferably alkali metal hydroxides, such as sodium hydroxide, ammonium hydroxide, and hydroxyalkyl amine salts. The term "higher alkyl" refers to chain lengths from about 8 and up. Examples of some preferred anionic surface active agents employed according to the present invention includes sodium lauryl ether sulfate, linear alkylbenzene sulfonates, and sodium lauryl sulfonate. Mixtures of anionic surface active agents can be employed when desired.

The nonionic surface active agent is combined with that amount of the anionic surface active agent which provides an overall composition denoted as "minimally irritating" the eye in accordance with the Draize test. Maximum eye irritation scores from 1 to about 18 are classified as conforming to this category of irritation. The general method for evaluating and scoring an accordance with this test is outlined in the Journal Pharmacology and Exp. Ther. 82, pg. 337 (1944) as well as in Section 191.12 of Federal Hazardous Substance Act. The ratio of nonionic to the anionic surface active agent for achieving the indicated level of irritation is at least about one part by weight of the nonionic surface active agent to one part by weight of the anionic surface agent. This minimum ratio is applicable for those compositions devoid of a foam stabilizer in either the form of an amine oxide or an alkanolamide. The applicable maximum ratio of nonionic surface active agents to anionic surface agent depends mainly on the detergency and/or viscosity considerations and is usually about 4:1 respectively.

The inclusion of a foam stabilizer of the amide type has the effect of increasing the eye irritation characteristics of the system beyond that normally to be expected. However, this increase can be compensated for by moderately increasing the minimal ratio of nonionic surface active agent to anionic surface active agent. The amine oxide foam stabilizers do not require increased amounts of the nonionic surface active agent. Generally, the amount of foam stabilizer is based upon the amount of the anionic surface active agent component present in the system, such being from about 10 to about 30% and preferably from about 20 to about 25% by weight of the anionic surface active component. Amounts of the foam stabilizer less than the specified lower limit results in less than optimum foam stabilizer characteristics. On the other hand, amounts of the stabilizer in excess of the higher limits specified is normally to be avoided because of the rinsing problems arising through the presence of such excessive amounts of the stabilizer. Thus, within the indicated range of the stabilizer content a minimum ratio of about 1 part by weight of the nonionic surface active agent to 1 part by weight of the total of the anionic surface active agent and foam stabilizer provide an overall composition having a mean eye irritation score in the "minimally" category. When the foam stabilizer is an alkanolamide, the minimum ratio of the nonionic surface active agent to the total of the anionic surface active agent and alkanolamide is about 2:1. When a foam stabilizer, such as an amine oxide and/or alkanolamide, is employed, the maximum ratio of nonionic surface active agent to total of anionic surface active agent and foam stabilizer is up to about 5:1.

Aqueous compositions employing the mixture of surface active agents of the present invention generally have solid contents of at least about 10% and generally up to about 45% by weight. Preferably such compositions have solid contents from about 15 to about 30% by weight. The compositions of the present invention can also include auxiliary ingredients such as thickeners, dyes, perfumes, preservatives, pH adjusters (e.g. citric acid); lather enhancers (e.g. about 3% by weight of an amphoteric surface active agent). Furthermore, the compositions of the present invention can contain mixtures of the ethylene oxide adducts required by the present invention with ethylene oxide adducts outside the scope of those required by the present invention. The relative amounts of such to obtain high viscosity type products can vary widely with the amounts readily ascertainable by those skilled in the art without undue experimentation once they are familiar with the present disclosure. The obtaining of high viscosity type detergent products not only depends upon the specific adducts employed and their relative amounts to each other, but also upon such parameters as total solids and types of other ingredients in the composition. The preferred aqueous compositions of the present invention have viscosities of at least about 10,000 centipoises, and most preferably about 10,000 to about 20,000 centipoises measured with a No. 4 spindle at 12 rpm. Also, the compositions generally have a pH of less than about 8.5, and preferably less than about 8.0.

The following nonlimiting examples are presented to further illustrate the present invention wherein all parts are by weight unless the contrary is stated. Examples I and II illustrate in detail a preferred method in which the nonionic surface active agents useful in the practice of the present invention can be prepared. Examples III–X illustrate some detergent compositions employing same.

EXAMPLE 1

Preparation of Ethoxylated Glycerol Tallowate

In a suitable reaction vessel are charged about one mole of tallow, about 1.05 mole of glycerine, and about 2.7 parts of potassium hydroxide. With stirring, the reaction mixture was heated to 100° C. and held for about one hour under 20 mm vacuum. The reaction mixture was then heated to about 165° C. with a nitrogen sparge and held for 3 hours. The product is a mixture of tallow mono- and diglycerides.

To a pressure vessel is charged about 1 mole of the above mono- and diglyceride mixture. The reactor is purged twice with nitrogen and heated to about 150° C. About 80 moles of ethylene oxide are added over an 8 hour period while maintaining the temperature at about 150° C. Upon the cooling of the reaction mixture to about 110° C., 25% aqueous sulphuric acid is added for neutralization to a pH of about 8 and the reaction mixture is then filtered. The product is a hard solid having a melting point of about 41° C., a Gardner color of 2, a HLB No. of 18±1, exhibits a pH of 1% solution in distilled water of about 7.0 and has a $LD_{50}$ of greater than 10 grams per kilogram of body weight when tested on young male adult albino rats of the Sprague Dawley strain.

The product of this example is tested for surface tension and interfacial tension in distilled water at 23° C., according to ASTM D 1331-56 (surface tension of water 72.3; interfacial tension of water vs. nujol=31.3). The results are as follows:

| Surface Tension (dynes/cm) | |
|---|---|
| Percent Concentration | |
| 1.0 | 49.7 |
| 0.1 | 49.5 |
| 0.025 | 51.4 |
| 0.01 | 55.2 |

| Interfacial Tension (dynes/cm; nujol) | |
| --- | --- |
| Percent Concentration | |
| 1.0 | 14.5 |
| 0.1 | 15.5 |
| 0.025 | 15.5 |
| 0.01 | 19.1 |

The product is also tested for Ross-Miles from heights both in distilled water and 150 ppm hard water at 23° C. according to ASTM D 1173 at 1.0 percent solids concentration. The results obtained are as follows:

| | Initial | 5 minute |
| --- | --- | --- |
| Distilled water | 75 mm | 55 mm |
| 150 ppm hard water | 65 mm | 32 mm |

The product shows zero scores for skin and eye irritation in tests for primary skin irritation and Draize Eye Irritation at the 100% active level and in 5.0% aqueous dispersion.

EXAMPLE II

An ethoxylated glycerol tallowate is obtained by a process similar to that discussed hereinabove wherein about 200 moles of ethylene oxide per mole of the mono- and diglyceride mixture are employed. The product is a hard solid having a melting point of about 53° C., a Gardner color of 2, a HLB No. of 19±1, a pH of 1% solution in distilled water of about 7.0, and has a $LD_{50}$ of greater than 10 grams per kilogram of body weight when tested on young male adult albino rats of the Spraque Dawley strain.

The product of this example is tested for surface tension and interfacial tension in distilled water at 23° C., according to ASTM D 1331-56 (surface tension of water 72.3; interfacial tension of water vs. nujol=31.3). The results are as follows:

| Surface Tension (dynes/cm) | |
| --- | --- |
| Percent Concentration | |
| 1.0 | 53.0 |
| 0.1 | 54.0 |
| 0.025 | 57.5 |
| 0.01 | 58.0 |

| Interfacial Tension (dynes/cm; nujol) | |
| --- | --- |
| Percent Concentration | |
| 1.0 | 17.0 |
| 0.1 | 18.3 |
| 0.025 | 18.0 |
| 0.01 | 23.1 |

The product is also tested for Ross-Miles from heights both in distilled water and 150 ppm hard water at 23° C. according to ASTM D 1173 at 1.0 percent solids concentration. The results obtained are as follows:

| | Initial | 5 minute |
| --- | --- | --- |
| Distilled water | 76 mm | 58 mm |
| 150 ppm hard water | 90 mm | 70 mm |

The product shows zero scores for skin and eye irritation in tests for primary skin irritation and Draize Eye Irritation at the 100% level and in 5.0% aqueous dispersion.

EXAMPLE III

A shampoo formulation is prepared containing about 8.44% by weight of the product of Example 1; about 5.80% by weight of an ethoxylated glycerol cocoate (i.e. Varonic L-63 available from Sherex) having 76% ethylene oxide in the molecule and an HLB number of about 15; and 14.4% by weight of sodium lauryl ether sulfate aqueous solution of 58–60% solids containing about 12–15% ethanol; about 10.22% by weight of cocoamidosulfobetaine available under the trade designation Varion CAS from Sherex, and about 61.14% by weight of deionized water. The viscosity of the formulation is about 13,500 centipoises at 12 rpm with a No. 4 Spindle. Upon dilution of the composition to 1.0% solids, the following Ross-Miles foam data is obtained as tested in accordance with the tests conducted in Examples I and II:

| | Initial | 5 minutes |
| --- | --- | --- |
| Deionized water | 217 mm | 190 mm |
| 150 ppm hard water | 231 mm | 202 mm |

EXAMPLE IV

A shampoo formulation is prepared containing about 6.03% by weight of the product of Example I; about 4.14% by weight of an ethoxylated glycerol cocoate (i.e. Varonic L-63 available from Sherex) having 76% ethylene oxide in the molecule and an HLB number of about 15; about 10.28% by weight of sodium lauryl ether sulfate aqueous solution of 58–60% solids containing about 12–15% by weight of ethanol; about 7.3% by weight of cocoamidosulfobetaine available under the trade designation Varion CAS from Sherex, and about 72.25% by weight of deionized water. The viscosity of the formulation is about 1920 centipoises at 12 rpm with a No. 4 spindle. Upon dilution of the composition to 1.0% solids, the following Ross-Miles foam data is obtained as tested in accordance with the tests conducted in Examples I and II:

| | Initial | 5 minutes |
| --- | --- | --- |
| Deionized water | 217 mm | 190 mm |
| 150 ppm hard water | 231 mm | 202 mm |

It is noted that the viscosity when using the product from Example I drops off greatly as total solids concentrations of less than about 15% by weight. Therefore, it is desirable for high viscosity formulation when using less than 15% by weight of total solids to employ the product of Example I along with an auxiliary thickener such as hydroxy ethyl cellulose.

EXAMPLE V

Shampoo compositions of 28.0% total solids containing the amounts of the product of Example I and of Varonic L-63 as shown in Table 1 hereinbelow, about 14.40% by weight of sodium lauryl ether sulfate aqueous solution of 60% solids having about 12-15% by weight of ethanol, about 10.22% by weight of Varion CAS, and deionized water to provide 100%:

TABLE 1

| Varonic LI-63 | Product of Example I | Viscosity (CPS) No. 4 Spindle at 12 rpm |
| --- | --- | --- |
| 14.24 | — | 40–50 |
| 10.68 | 3.56 | 340–380 |
| 7.12 | 7.12 | 6,500–6,800 |
| 3.56 | 10.68 | 42,000–43,000 |
| — | 14.24 | >100,000 |

EXAMPLE VI

A shampoo formulation is prepared containing about 7.5% by weight of the product of Example II; about 10.0% by weight of sodium lauryl ether sulfate aqueous solution containing 58–60% and having about 12–15% by weight ethanol, about 1.40% by weight of cocoamidosulfobetaine available under the trade designation Varion CAS from Sherex, about 2% by weight of dihydroxyethyl $C_{12}$-$C_{15}$ ether amine oxide available from Sherex under the trade designation Varox 185E, and about 79.10% by weight of deionized water. The viscosity of the formulation is about 11,400 centipoises at 12 rpm with a No. 4 Spindle. Upon dilution of the composition to 1.0% solids, the following Ross-Miles foam data is obtained as tested in accordance with the tests conducted in Examples I and II:

|  | Initial | 5 minutes |
| --- | --- | --- |
| Deionized water | 220 mm | 193 mm |
| 150 ppm hard water | 230 mm | 202 mm |

EXAMPLE VII

A shampoo formulation is prepared containing about 7.12% by weight of the product of Example II; about 7.12% by weight of an ethoxylated glycerol cocoate (i.e. Varonic L-63 available from Sherex) having 76% ethylene oxide in the molecule and an HLB number of about 15; about 14.4% by weight of sodium lauryl ether sulfate aqueous solution containing 58–60% solids and having about 12 to 15% by weight of ethanol, about 10.22% by weight of cocoamidosulfobetaine available under the trade designation Varion CAS from Sherex, and about 61.14% by weight of deionized water. The viscosity of the formulation is about 1800 centipoises at 12 rpm with a No. 4 Spindle. Upon dilution of the composition to 1.0% solids, the following Ross-Miles foam data is obtained as tested in accordance with the tests conducted in Examples I and II:

|  | Initial | 5 minutes |
| --- | --- | --- |
| Deionized water | 219 mm | 195 mm |
| 150 ppm hard water | 232 mm | 201 mm |

EXAMPLE VIII

Shampoo formulations of 28% solids containing the product of Example II and/or Varonic LI-63 in the amounts set forth in Table II below; about 14.40% by weight of sodium lauryl ether sulfate aqueous solution having 60% solids and having about 12 to about 15% by weight of ethanol, about 10.22% by weight of cocoamidosulfobetaine available under the trade designation Varion CAS from Sherex, and water to provide 100%:

TABLE 2

| Varonic LI-63 | Product of Example II | Viscosity (CPS) No. 4 Spindle at 12 rpm |
| --- | --- | --- |
| 14.24 | 0 | 40–50 |
| 10.68 | 3.56 | 150–190 |
| 7.12 | 7.12 | 1,600–1,900 |
| 3.56 | 10.68 | 12,000–12,500 |
| 0 | 14.24 | >100.000 |

EXAMPLE IX

A shampoo formulation is prepared containing about 9.38% by weight of the product of Example II, about 4.69% by weight of sodium lauryl ether sulfate aqueous solution containing 58–60% and having about 12 to about 15% by weight of ethanol; about 0.94% by weight of cocoamidosulfobetaine available under the trade designation Varion CAS from Sherex; and 84.99% by weight of deionized water. The viscosity of the formulations is about 23,500 centipoises at 12 rpm with a No. 4 spindle.

EXAMPLE X

A shampoo formulation is prepared containing about 12.50% by weight of the product of Example II, about 6.20% by weight of sodium lauryl ether sulfate aqueous solution containing 58–60% and having about 12–15% by weight of ethanol; about 1.30% by weight of cocoamidosulfobetaine available under the trade designation Varion CAS from Sherex; and about 80.00% by weight of deionized water. The viscosity of the formulation is about 82,500 centipoises at 12 rpm with a No. 4 spindle.

It has been noted that the viscosity limits of the product of Example II drops off at concentrations of about 10%. In shampoo formulations where total solids are less than this, it is suggested that if high viscosity is desired, an auxiliary thickener such as hydroxy ethyl cellulose be employed along with the product of Example II.

What is claimed is:

1. A detergent composition having low eye and skin irritation properties and capable of forming a high viscosity composition in water when the solids content is at least about 10% by weight comprising:
   (a) adduct of ethylene oxide or mixtures of ethylene oxide and propylene oxide and a partial glycerol ester of a carboxylic fatty acid; wherein at least about 50% of said fatty acids have at least 16 carbon atoms, and wherein said adduct is from at least about 50 moles of ethylene oxide per mole of said glycerol ester; and provided that said adduct is from at least about 70 moles of ethylene oxide per mole of said glycerol ester when a mixture of ethylene oxide and propylene oxide containing less than about 85 mole percent of ethylene oxide based on the total of ethylene oxide and propylene oxide is employed; and (b) anionic surface active agent, wherein the weight ratio of (a) to (b) is about 1:1 to about 4:1, respectively, and wherein said anionic surface-active agent is selected from the group of salts of higher alkyl sulfates, salts of higher alkyl ether sulfates, salts of higher alkyl benzene sulfonates, salts of higher alkyl sulfonates, and mixtures thereof.

2. The composition of claim 1 wherein said adduct is an adduct of ethylene oxide and said partial glycerol ester.

3. The composition of claim 1 wherein said adduct is from at least about 60 moles of ethylene oxide per mole of said glycerol ester.

4. The composition of claim 1 wherein said adduct is from at least about 80 moles of ethylene oxide per mole of said glycerol ester.

5. The composition of claim 1 wherein said adduct is from at least about 100 moles of ethylene oxide per mole of glycerol ester.

6. The composition of claim 1 wherein said adduct is from up to about 1000 moles of ethylene oxide per mole of glycerol ester.

7. The composition of claim 1 wherein said adduct is from up to about 500 moles of ethylene oxide per mole of glycerol ester.

8. The composition of claim 1 wherein said adduct is from about 80 moles to about 200 moles of ethylene oxide per mole of glycerol ester.

9. The composition of claim 1 wherein said mixtures contain a mole ratio of ethylene oxide to propylene oxide of about 2:1 to about 4.5:1.

10. The composition of claim 1 wherein at least about 50% by weight of said fatty acids have at least 18 carbon atoms.

11. The composition of claim 1 wherein the fatty acids have carbon atoms no greater than 22.

12. The composition of claim 1 wherein the fatty acids are obtained from tallow oil.

13. The composition of claim 1 wherein said fatty acids are from hydrogenated tallow oil.

14. The composition of claim 1 wherein said partial glycerol ester has a monoglyceride content of from about 15 to about 45 weight percent with diglyceride essentially constituting the balance.

15. The composition of claim 14 wherein said monoglyceride content is about 25 to about 35% by weight.

16. The composition of claim 1 wherein said anionic surface active agent is selected from the group of sodium lauryl sulfate, sodium lauryl ether sulfate, sodium $C_{12}-C_{18}$ alkyl benzene sulfonate, or sodium lauryl sulfonate.

17. A detergent composition having low eye and skin irritation properties and capable of forming a high viscosity composition in water when the solids content is at least about 10% by weight comprising:

(a) adduct of ethylene oxide or mixtures of ethylene oxide and propylene oxide and a partial glycerol ester of a carboxylic fatty acid; wherein at least about 50% of said fatty acids have at least 16 carbon atoms, and wherein said adduct is from at least about 50 moles of ethylene oxide per mole of said glycerol ester; and provided that said adduct is from at least about 70 moles of ethylene oxide per mole of said glycerol ester when a mixture of ethylene oxide and propylene oxide containing less than about 85 mole percent of ethylene oxide based on the total of ethylene oxide and propylene oxide is employed;

(b) anionic surface active agent selected from the group of salts of higher alkyl sulfates, salts of higher alkyl ether sulfates, salts of higher alkyl benzene sulfonates, salts of higher alkyl sulfonates, and mixtures thereof;

(c) a foam stabilizing agent wherein the amount of foam stabilizing agent is from about 10 to about 30% by weight of the anionic surface-active agent (b), and wherein the weight ratio of (a) to the total of (b) and (c) is about 1:1 to about 5:1, respectively.

18. The composition of claim 17 wherein said foam stabilizing agent is an amine oxide.

19. The composition of claim 17 wherein said foam stabilizing agent is an alkanol amide, and wherein the mole ratio of (a) to total of (b) and (c) is at least about 2:1.

20. The composition of claim 17 wherein said anionic surface active agent is selected from the group of sodium lauryl sulfate, sodium lauryl ether sulfate, sodium $C_{12}-C_{18}$ alkyl benzene sulfonate, or sodium lauryl sulfonate.

21. The composition of claim 17 wherein said partial glycerol ester has a monoglyceride content of from about 15 to about 45 weight percent with diglyceride essentially constituting the balance.

22. The composition of claim 21 wherein said monoglyceride content is about 25 to about 35% by weight.

23. The composition of claim 17 wherein said adduct is an adduct of ethylene oxide and said partial glycerol ester.

24. The composition of claim 17 wherein said adduct is from at least about 60 moles of ethylene oxide per mole of said glycerol ester.

25. The composition of claim 17 wherein said adduct is from at least about 80 moles of ethylene oxide per mole of said glycerol ester.

26. The composition of claim 17 wherein said adduct is from at least about 100 moles of ethylene oxide per mole of glycerol ester.

27. The composition of claim 17 wherein said adduct is from up to about 1000 moles of ethylene oxide per mole of glycerol ester.

28. The composition of claim 17 wherein said adduct is from up to about 500 moles of ethylene oxide per mole of glycerol ester.

29. The composition of claim 17 wherein said adduct is from about 80 moles to about 200 moles of ethylene oxide per mole of glycerol ester.

30. The composition of claim 17 wherein said mixtures contain a mole ratio of ethylene oxide to propylene oxide of about 2:1 to about 4.5:1.

31. The composition of claim 17 wherein at least about 50% by weight of said fatty acids have at least 18 carbon atoms.

32. The composition of claim 17 wherein the fatty acids have carbon atoms no greater than 22.

33. The composition of claim 17 wherein the fatty acids are obtained from tallow oil.

34. The composition of claim 17 wherein said fatty acids are from hydrogenated tallow oil.

35. An aqueous detergent composition having a viscosity of at least about 10,000 centipoises at room temperature (No. 4 spindel at 12 rpm) and comprising water and the composition of claim 1 and having a solids content of at least about 10% by weight.

36. The composition of claim 35 which has a viscosity of about 10,000 to about 20,000 centipoises.

37. The composition of claim 35 which has a solids content of up to about 45% by weight.

38. The composition of claim 35 which has a solids content of from about 15 to about 30% by weight.

39. The composition of claim 35 which has a pH of less than about 8.5.

40. The composition of claim 35 wherein said adduct is from at least about 80 moles of ethylene oxide per mole of said glycerol ester.

41. The composition of claim 35 wherein said monoglyceride content is about 25 to about 35% by weight.

42. The composition of claim 35 wherein at least about 50% by weight of said fatty acids have at least 18 carbon atoms.

43. The composition of claim 35 wherein the fatty acids are obtained from tallow oil.

44. The composition of claim 35 wherein said fatty acids are from hydrogenated tallow oil.

45. The composition of claim 35 wherein said anionic surface active agent is selected from the group of sodium lauryl sulfate, sodium lauryl ether sulfate, sodium $C_{12}$–$C_{18}$ alkyl benzene sulfonate, or sodium lauryl sulfonate.

46. An aqueous detergent composition having a viscosity of at least about 10,000 centipoises at room temperature (No. 4 spindle at 12 rpm) and comprising water and the composition of claim 17 and having a solids content of at least about 10% by weight.

47. The composition of claim 46 which has a viscosity of about 10,000 to about 20,000 centipoises.

48. The composition of claim 46 which has a solids content of up to about 45% by weight.

49. The composition of claim 46 which has a solids content of from about 15 to about 30% by weight.

50. The composition of claim 46 which has a pH of less than about 8.5.

51. The composition of claim 46 wherein said adduct is from at least about 80 moles of ethylene oxide per mole of said glycerol ester.

52. The composition of claim 46 wherein said monoglyceride content is about 25 to about 35% by weight.

53. The composition of claim 46 wherein at least about 50% by weight of said fatty acids have at least 18 carbon atoms.

54. The composition of claim 46 wherein the fatty acids are obtained from tallow oil.

55. The composition of claim 46 wherein said fatty acids are from hydrogenated tallow oil.

56. The composition of claim 46 wherein said anionic surface active agent is selected from the group of sodium lauryl sulfate, sodium lauryl ether sulfate, sodium $C_{12}$–$C_{18}$ alkyl benzene sulfonate, or sodium lauryl sulfonate.

* * * * *